US011786544B2

(12) United States Patent
Kennovin et al.

(10) Patent No.: US 11,786,544 B2
(45) Date of Patent: Oct. 17, 2023

(54) FORMULATIONS OF PHOSPHORAMIDATE DERIVATIVES OF NUCLEOSIDE DRUGS

(71) Applicant: NuCana plc, Edinburgh (GB)

(72) Inventors: Gordon Kennovin, Edinburgh (GB); Hugh Griffith, Edinburgh (GB)

(73) Assignee: NuCana plc, Edinburgh (GB)

( * ) Notice: Subject to any disclaimer, the term of this patent is extended or adjusted under 35 U.S.C. 154(b) by 0 days.

(21) Appl. No.: 17/231,606

(22) Filed: Apr. 15, 2021

(65) Prior Publication Data

US 2022/0031728 A1 Feb. 3, 2022

Related U.S. Application Data

(63) Continuation of application No. 16/065,402, filed as application No. PCT/GB2016/054025 on Dec. 21, 2016, now abandoned.

(30) Foreign Application Priority Data

Dec. 23, 2015 (GB) ...................... 1522764

(51) Int. Cl.
| | | |
|---|---|---|
| A01N 43/04 | (2006.01) |
| A61K 31/70 | (2006.01) |
| A61K 31/7076 | (2006.01) |
| A61K 9/00 | (2006.01) |
| A61K 47/18 | (2017.01) |
| A61K 47/20 | (2006.01) |
| A61K 9/08 | (2006.01) |
| A61K 31/7072 | (2006.01) |
| A61P 35/02 | (2006.01) |
| A61K 47/22 | (2006.01) |

(52) U.S. Cl.
CPC ........ *A61K 31/7076* (2013.01); *A61K 9/0019* (2013.01); *A61K 9/08* (2013.01); *A61K 31/7072* (2013.01); *A61K 47/18* (2013.01); *A61K 47/20* (2013.01); *A61K 47/22* (2013.01); *A61P 35/02* (2018.01)

(58) Field of Classification Search
None
See application file for complete search history.

(56) References Cited

U.S. PATENT DOCUMENTS

| | | | |
|---|---|---|---|
| 8,492,400 B2 | 7/2013 | Mudumba et al. |
| 8,609,627 B2 | 12/2013 | Cho et al. |
| 8,658,667 B2 | 2/2014 | Mudumba et al. |
| 8,759,318 B2 | 10/2014 | Smith et al. |
| 8,871,737 B2 | 10/2014 | Smith et al. |
| 8,933,053 B2 | 1/2015 | McGuigan et al. |
| 9,173,893 B2 | 11/2015 | Cho et al. |
| 9,221,866 B2 | 12/2015 | McGuigan et al. |
| 9,278,990 B2 | 3/2016 | Smith et al. |
| 9,655,915 B2 | 5/2017 | McGuigan et al. |
| 10,022,390 B2 | 7/2018 | McGuigan et al. |
| 10,993,957 B2 | 5/2021 | McGuigan et al. |
| 11,400,107 B2 | 8/2022 | Griffith et al. |
| 11,414,451 B2 | 8/2022 | Kotala et al. |
| 11,414,452 B2 | 8/2022 | Griffith et al. |
| 11,559,542 B2 | 1/2023 | McGuigan et al. |
| 2007/0203173 A1 | 8/2007 | Mudumba et al. |
| 2008/0096967 A1 | 4/2008 | Lopez et al. |
| 2009/0022803 A1 | 1/2009 | Lopez et al. |
| 2010/0249068 A1 | 9/2010 | Beigelman et al. |
| 2012/0040924 A1 | 2/2012 | Cho et al. |
| 2012/0052046 A1* | 3/2012 | Chamberlain .......... A61P 31/12 424/85.4 |
| 2012/0071424 A1 | 3/2012 | Smith et al. |
| 2014/0286903 A1 | 9/2014 | Chamberlain et al. |
| 2015/0352118 A1 | 12/2015 | Goris et al. |
| 2020/0181186 A1 | 6/2020 | Griffith et al. |
| 2020/0345755 A1 | 11/2020 | Griffith et al. |
| 2022/0402962 A1 | 12/2022 | Griffith et al. |

FOREIGN PATENT DOCUMENTS

| | | | |
|---|---|---|---|
| CL | 202398 | 8/1997 |
| CL | 7302 | 1/2001 |
| WO | WO 2000/71163 A1 | 11/2000 |
| WO | WO 2005/120453 A1 | 12/2005 |
| WO | WO 2006/081363 A2 | 8/2006 |
| WO | WO 2006/100439 A1 | 9/2006 |
| WO | WO 2007/092620 A2 | 8/2007 |
| WO | WO 2010/081082 A2 | 7/2010 |
| WO | WO 2010/091386 A2 | 8/2010 |
| WO | WO 2010/108140 A1 | 9/2010 |
| WO | WO 2012/040127 A1 | 3/2012 |
| WO | WO 2012/117246 A1 | 9/2012 |
| WO | WO-2012117246 A1 * | 9/2012 | ........... A61K 31/675 |
| WO | WO 2013/070887 A1 | 5/2013 |
| WO | WO 2013/107515 A1 | 7/2013 |
| WO | WO 2014/004895 A1 | 1/2014 |
| WO | WO 2014/164754 A1 | 10/2014 |
| WO | WO 2015/198059 A1 | 12/2015 |
| WO | WO 2016/083830 A1 | 6/2016 |

OTHER PUBLICATIONS

Vemula et al. International Journal of Pharmaceutical Sciences Review and Research (2010), vol. 5, pp. 41-51.*
Vescia, S., et al. "Management of venous port systems in oncology: a review of current evidence." Annals of Oncology 19.1 (2008): 9-15.*
U.S. Appl. No.17/878,747, Griffith et al., filed Aug. 1, 2022.
U.S. Appl. No.18/095,937, McGuigan et al., filed Jan. 11, 2023.
(Continued)

*Primary Examiner* — Patrick T Lewis
(74) *Attorney, Agent, or Firm* — Knowles Intellectual Property Strategies, LLC

(57) ABSTRACT

This invention relates to pharmaceutical formulations and formulation strategies of protides (phosphoramidate derivatives of nucleosides) and, in particular, protides useful in the treatment of cancer such as NUC-3373 (5-fluoro-2'-deoxyuridine-5'-O-[1-naphthyl (benzoxy-L-alaninyl)] phosphate) and NUC-7738 (3'-deoxyadenosine-5'-O-[phenyl(benzyloxy-L-alaninyl)] phosphate). In particular, the invention relates to formulations which comprise a polar aprotic solvent, for example dimethyl acetamide (DMA).

9 Claims, No Drawings

(56) References Cited

OTHER PUBLICATIONS

Anonymous: "protide-definition of protide in English Oxford Dictionaries," pp. 1-3 (Feb. 15, 2017).
Blanka Gönczy; "Design, Synthesis and Biological Evaluation of Nucleotide Pro-drugs Centred on Clinically Active Anticancer Nucleosides," Thesis of Cardiff School of Pharmacy and Pharmaceutical Sciences Cardiff University; 2016.
Blagden et al., "Abstract CT028: First-in-human phase I study of the nucleotide analogue NUC-3373 designed to overcome fluoropyrimidine drug resistance mechanisms," Cancer Research, (2016) http://cancerres.aacrioujournals.org/content/76/14_Supplement/CT028.
Blagden et al., "First-in-human phase I study of NUC-3373, a nucleotide analogue designed to overcome fluoropyrimidine drug resistance mechanisms," AACR 2016.
Cahard, D. et al., "Aryloxy Phosphoramidate Triesters as Pro-Tides," Mini-Reviews in Medicinal Chemistry, 2004, 4, DD. 371-382.
Cancer [online], [retrieved on Jul. 6, 2007] Retrieved from the Internet, URL: http://www.nlm.nih.gov/medlineplus/cancer.html.
Chopra et al. "Plant tumour biocontrol agent employs a tRNA-dependent mechanism to inhibit leucyl-tRNA synthetase," Nature Communications, 4:1417 (2013).
Ciccolini J. et al.; Thymidine phosphorylase and fluoropyrimidines efficacy: a Jekyll and Hyde story. Curr Med Chem Anticancer Agents 2004; 4:71-81.
Congiata C. et al.; Novel potential anticancer naphthyl phosphoramidates of BVdU: separation of diastereoisomers and assignment of the absolute configuration of the phosphorus center. J. Med. Chem. 2006; 49:452-5.
Congiatu, Costantino; et al., "Design, Synthesis and Biological Evaluation of Some Novel Nucleotide Prodrugs as Potential Anticancer Agents," A Thesis submitted to the University of Wales for the Degree of Philosophiae Doctor, 2006; p. 1-290.
Dang, Q. et al., Discovery of potent and specific fructose-1,6-biphosphate inhibitors and a series of orally-bioavailable phosphoramidase-sensitive prodrugs for the treatment of type 2 diabetes. J. Am. Chem. Soc. 2007,129, pp. 15494-15502.
De Bruin M. et al.; Role of platelet derived endothelial cell growth factor thymidine phosphorylase in fluoropyrimidine sensitivity and potential role of deoxyribose-1-phosphate. Nucleosides Nucleotides Nucleic Acids 2004; 23:1485-90.
Derudas, M. et al, The Application of Phosphoramidate Protide Technology to Acyclovir Confers Anti-HIV Inhibition. J. Med. Chem. 2009, 52, pp. 5520-5530.
Galmarini C.M. et al.; Nucleoside analogues and nucleobases in cancer treatment. Lancet Oncol 2001; 3:415-24.
Gao et al. Growing Crystalline Zinc-1,3,5-benzenetricarboxylate Metal-Organic Frameworks in Different Surfactants. Inorganic Chemistry (2014), vol. 53, pp. 691-693.
Ghazaly et al., "Abstract B46: NUC-3373: A novel pyrimidine nucleotide analogue that overcomes key cancer drug resistance limiting patient survival," Molecular Cancer Therapeutics, http://mct.aacrjoumals.org/content/14/12 supplement 2/B46 (2015).
Ghazaly et al., NUC-3373: A novel pyrimidine nucleotide analogue that overcomes key cancer drug resistance limiting patient survival, AACR 2015.
Ghazaly, E. et al. Interim pharmacokinetic and pharmacodynamic data from the first-in-human study of NUC-3373, a pyrimidine nucleotide analogue, in patients with advanced solid tumours, esmo Poster, Sep. 2017.
Golub et al., Molecular Classification of Cancer: Class Discovery and Class Prediction by Gene Expression Monitoring, Science (1999), vol. 286, 531-537.
Goossens, G. A. (2015). Flushing and locking of venous catheters: Available evidence and evidence deficit. Nursing Research and Practice, 2015 doi:http://dx.doi.org/10.1155/2015/985686.
Grem JL. 5-Fluorouracil: forty-plus and still ticking. A review of its preclinical and clinical development. Invest New Drugs. Nov. 2000;18(4):299-313.
Griffith, et al.; "Enhanced inhibition of the EDHF phenomenon by a phenyl methoxyalaninyl phosphoramidate derivative of dideoxyadenosine," British Journal of Pharmacology, vol. 142, No. 1, pp. 27-30, May 2004.
Guidance for Industry (Food and Drug administration; 2005 (hereafter referred as FDA).
Harris S.A., McGuigan C., Andrei G., Snoeck R., De Ce., Balzarini J., Synthesis and antiviral evaluation of phosphoramidate derivatives of (E)-5-(2-bromovinyl)-2'deoxyuridine. Antivir Chem Chemother 2002; 12:293-300.
Hatse S., De C.E., Balzarini J., Role of antimetabolites of purine and pyrimidine nucleotide metabolism in tumor cell differentiation. Biochem Phannacol 1999; 58:539-55.
Hecker S.J. and Erion M.D., Prodrugs of phosphates and phosphonates. J. Med. Chem. 2008; 51:2328-45.
Heidelberger, C. et al., Fluorinated pyrimidines, a new class of tumor-inhibitory compounds. Nature 1957,179, pp. 663-666.
Holland, J. F.; Frei, E.; Pizzomo, G.; Diasio, R. B.; Cheng, Y. C.: "Cancer Medicine" 7th Ed. BC Decker: Hamilton, Ontario, Canada, 2006.
Homsi, J. et al., "Hepatic Arterial Infusion of Chemotherapy for Hepatic Metastases From Colorectal Cancer," Cancer Control, 13(1):42-47 (2006).
International Search Report and Written Opinion for International application PCT/GB2016/054025 dated Mar. 3, 2017; 6 pages.
Ishikawa T., Utoh M., Sawada N., Nishida M., Fukase Y, Sekiguchi F., Ishitsuka H., Tumor selective delivery of 5-fluorouracil by capecitabine, a new oral fluoropyrimidine carbamate, in human cancer xenografts. BiochemPhannacol 1998; 55: 1091-7.
Jette L. et al.; Resistance of colorectal cancer cells to 5-FUDR and 5-FU caused by Mycoplasma infection. Anticancer Res 2008; 28:2175-80.
Kamoshida S., et al.; Immunohistochemical demonstration of fluoropyrimidine-metabolizing enzymes in various types of cancer. Oncol Rep. 2005.14: 1223-30.
Kidder M., Chan P.I., Seraj l,M., Patton W,C., King "A Assessment of archived paraffin-embedded cervical condyloma tissues for mycoplasma-conserved DNA using sensitive PCR-ELISA," Gynecol Oncol 1998; 71:254-257.
Kinsella A.Rand Smith D., Tumor resistance to anti metabolites. Gen Pharmacol 1998; 30:623-6.
Krishna G. et al. Permeability of lipophilic compounds in drug discovery using in-vitro human absorption model, Caco-2. Int J Pharm. Jul. 3, 2001;222(1):77-89.
Lala et al.; Role of nitric oxide in tumor progression: Lessons from experimental tumors, Cancer and Metastasis Reviews (1998), 17,91-106.
Lee, W. A. et al., Antimicrob Agents Chemother. 2005, 49, pp. 1898-1906.
Liu Ang, et al.; "Challenges and solutions in the bioanalysis of BMS-986094 and its metabolites including a highly polar, active nucleoside triphosphate in plasma and tissues using LC-M", Journal of Chromatagraphy B: Biomedical Sciences & Applications, Elsevier, Amsterdam, vol. 1000, pp. 29-40 (2015).
Longley D.B. et al.; 5-fluorouracil: mechanisms of action and clinical strategies. Nat Rev Cancer 2003; 3:330-8.
McGuigan Christopher et al.; Phosphoramidate ProTides of 2'-Cmethy lguanosine as highly potent inhibitors of hepatitis C vims. Study of their in vitro and in vivo properties. J Med Chem 2010; 53:4949-57.
McGuigan, C. et al.; "Design, synthesis and evaluation of a novel double pro-drug: INX-08189. A new clinical candidate for hepatitis C virus," Bioorg. Med. Chem. Lett. 2010, 20 pp. 4850-4854.
McGuigan, C.; Tsang, H. W.,; Cahardr, D. Turner, K.; Velazquez, S.; Salgado, A; Bidois, L.; Naesens, L.; De Clercq, E.; Balzarini, J. Phosphoramidate derivatives of d4T as inhibitors of HIV: The effect of amino acid variation. Antiviral Res. 1997, 35, 195.
McGuigan, Christopher, Thiery, Jean-Christophe, Daverio, Felice. Davies, Gaynor, Mason, Malcolm, Anti-cancer ProTides: tuning the activity of BVDU phosphoramidates related to thymectactin, Bioorganic & Medicinal Chemistry, 2005, vol. 13(9) DD.3219-3227.
McGuigan et al.; Phosphoramidate derivatives of AZT as inhibitors of HIV: studies on the carboxyl terminus, Antiviral Chemistry & Chemotherapy, 1993; 4:97-101.

(56) References Cited

OTHER PUBLICATIONS

McGuigan, C.; Pathiran'a, R. N.; Balzarini, J.; De Clercq, E. Intracellular delivery of bioactive AZT nucleotides by aryl phosphate derivatives of AZT. Med. Chem. 1993; 36, 1048.

McGuigan et al.; Synthesis and Evaluation of some masked phosphate esters of the anti-herpesvirus drug 882C (Netivudine) as potential antiviral agents, Antiviral Chemistry & Chemotheraphy, 1998, 9:233-243.

McGuigan, C. et al.; "Application of phosphoramidate pronucleotide technology to abacavir leads to a significant enhancement of antiviral potency," J. Med. Chem. 2005, 48, pp. 3504-3515.

McGuigan, C. et al.; Phosphoramidate ProTides of the anticancer agent FUDR successfully deliver the preformed bioactive monophosphate in cells and confer advantage over the parent nucleoside; Journal of Medicinal Chemistry vol. 54, No. 20 pp. 7247-7258 (2011).

McGuigan, C.; et al.; "Aryl phosphora'midate derivatives of d4T have improved anti-HIV efficacy in tissue vulture and may act by the generation of a novel intracellular metabolite". J. Med. Chem. 1996, 39, 1748.

McIntee et al.; Amino Acid Phosphoramidate Nucleosides: Potential ADEPT/GDEPT substrates, Bioorganic & Medicinal Chemistry Letters, 2001, 11:2803-2805.

Mehellou, J. et al.; Aryloxy phosphoramidate triesters: a technology for delivering mono-phosphorylated nucleosides and sugars into cells. Chem. Med. Chem., 2009, 4, 11, 1779.

Mehellou, Y. et al.; Phosphoramidates of 2'-B-d-arabinouridine (AraU) as phosphate prodrugs: design, synthesis, in vitro activity and metabolism. Bioorg. Med. Chem. 2010, 18, 2439.

Moertel C.G., Chemotherapy for colorectal cancer. N Engl J Med 1994; 330: 1136-42.

Murakami Y., et al.; Different mechanisms of acquired resistance to fluorinated pyrimidines in human colorectal cancer cells. Int J Oncol, 2000; 17:277-83.

Nakumura et al. Anticancer Research (2006), vol. 26, pp. 43-48.

NuCana Press Release. NuCana announces update for Phase 3 Biliary Tract Cancer Study. Edinburgh, U.K. Mar. 2, 2022.

Seedher N, Bhatia S. Solubility enhancement of Cox-2 inhibitors using various solvent systems. AAPS PharmSciTech. 2003;4(3):E33.

Seethala, R., & Fernandes, P. (Eds.). (2001). Handbook of Drug Screening (1st ed.). CRC Press, https://doi.org/10.1201/9780203908570.

Seethala, R., & Zhang, L. (2009). Handbook of Drug Screening (2nd ed.). Informa Healthcare.

Serpi et al., "Synthetic Approaches for the Preparation of Phosphoramidate Prodrugs of 2'-Deoxvoseudoisocvtidine," Chem Op 6(3):424-436 (2017).

Seno T., Ayusawa D., Shimizu K., Koyama H., Takeishi K., Hori T., Thymine-less death and genetic events in mammalian cells. Basic Life Sci 1985; 31 :241-63.

Sotos G.A., Grogan L., Allegra C.J., Preclinical and clinical aspects of biomodulation of 5-fluorouracil. Cancer Treat Rev 1994; 20:11-49.

Spears et al., "Thymidylate synthetase inhibition in malignant tumors and normal liver of patients given intravenous 5-fluorouracil," Cancer Research, 44:4144-4150 (1984).

Takiuchi et al., "Thymidylate synthase gene expression in primary tumors predicts activity of S-1-based chemotherapy for advanced gastric cancer," Gastrointestinal Cancer Research, 1(5):171-176 (2007).

Tanaka F., Fukuse T., Wada H., Fukushima M., The history, mechanism and clinical use of oral 5-fluorouracil derivative chemotherapeutic agents. Curr Phann Biotechnol. 2000; 1: 137-64.

Uyama et al., "Thymidylate synthase and dihydropyrimidine dehydrogenase expression and histological effects of preoperative UFT in gastric cancer patients," Gan To Kagaku Ryoho, 33(5):625-629 (2006).

Vande Voorde et al.; The Cytostatic Activity of NUC-3073, a Phosphoramidate Prodrug of 5-fluoro-2'-deoxyuridine, is Independent of Activation by Thymidine Kinase and Insensitive to Degradation by Phosphorlytic Enzymes; Biochemical Pharmacology; vol. 82, No. 5; Sep. 1, 2011; pp. 441-452.

Vijver et al., "Antibacterial 5'-0-(N-dipeptidyl)-sulfamoyladenosines," Bioorganic & Medicinal Chemistry, 17(1):260-269 (2009).

Bré J, et al. The novel anti-cancer fluoropyrimidine NUC-3373 is a potent inhibitor of thymidylate synthase and an effective DNA-damaging agent. Cancer Chemother Pharmacol. 2023.

Vescia, S. et al. Management of venous port systems in oncology: a review of current evidence, Annals of Oncology 19: 9-15, Jan. 2008.

Negreira N. et al. Multianalyte determination of 24 cytostatics and metabolites by liquid chromatography-electrospray-tandem mass spectrometry and study of their stability and optimum storage conditions in aqueous solution. TALANTA, Nov. 15, 2013;116:290-9.

Bilir A. Guneri A.D., Altinoz M.A.: Acetaminophen and DMSO modulate growth and gemcitabine cytotoxicity in FM3 A breast cancer cells in vitro, NEOPLASMA, vol. 51, No. 6. Jan. 1, 2004, pp. 460-464, XP055205686.

\* cited by examiner

FORMULATIONS OF PHOSPHORAMIDATE DERIVATIVES OF NUCLEOSIDE DRUGS

RELATED APPLICATIONS

This application is a continuation of U.S. patent application Ser. No. 16/065,402, filed Jun. 22, 2018; which is a § 371 national stage application based on Patent Cooperation Treaty Application serial number PCT/GB2016/054025, filed Dec. 21, 2016; which claims the benefit of priority to United Kingdom Patent Application No. GB 1522764.8, filed Dec. 23, 2015.

This invention relates to pharmaceutical formulations and formulation strategies of protides (phosphoramidate derivatives of nucleosides) and, in particular, protides useful in the treatment of cancer such as NUC-3373 (5-fluoro-2'-deoxyuridine-5'-O-[1-naphthyl (benzoxy-L-alaninyl)] phosphate), NUC-7738 (3'-deoxyadenosine-5'-O-[phenyl(benzyloxy-L-alaninyl)] phosphate) and CPF-448 (2-chloro-2'-beta-fluoro-2'-deoxyadenosine-5-[phenyl-(benzoxy-L-(alaninyl)]-phosphate). In particular, the invention relates to formulations which comprise a polar aprotic solvent, for example dimethyl acetamide (DMA).

BACKGROUND

Protides are masked phosphate derivatives of nucleosides. They have been shown to be particularly potent therapeutic agents in the fields of both antivirals and oncology. Protides, more specifically, are prodrugs of monophosphorylated nucleosides. These compounds appear to avoid many of the inherent and acquired resistance mechanisms which limit the utility of the parent nucleosides (see, for example, '*Application of Pro Tide Technology to Gemcitabine: A Successful Approach to Overcome the Key Cancer Resistance Mechanisms Leads to a New Agent (NUC-*1031) *in Clinical Development*'; Slusarczyk et al; *J. Med. Chem.*; 2014, 57, 1531-1542).

NUC-3373 (5-fluoro-2'-deoxyuridine-5'-O-[1-naphthyl (benzoxy-L-alaninyl)] phosphate) is a protide adaptation of 5FU/FUDR, the current foundation treatment against colorectal cancer. NUC-3373 and a range of related compounds have shown activity in vitro against a range of cancer models, in many cases and in particular for NUC-3373 that activity was outstanding and far superior to the results obtained with 5-fluorouracil. The addition of the protide phosphoramidate moiety to the 5-fluorouracil/FUDR molecule confers the specific advantages of delivering the key activated form of the agent (FdUMP) into the tumour cells. Non clinical studies have demonstrated that NUC-3373 overcomes the key cancer cell resistance mechanisms associated with 5-FU and its oral pro-drug capecitabine, generating high intracellular levels of the active FdUMP metabolite, resulting in a much greater inhibition of tumour cell growth. Furthermore, in formal dog toxicology studies, NUC-3373 is significantly better tolerated than 5-FU (see WO2012/117246; McGuigan et al.; *Phosphoramidate Pro Tides of the anticancer agent FUDR successfully deliver the preformed bioactive monophosphate in cells and confer advantage over the parent nucleoside; J. Med. Chem.*; 2011, 54, 7247-7258; and Vande Voorde et al.; *The cytostatic activity of NUC-3073, a phosphoramidate prodrug of 5-fluoro-2'-deoxyuridine, is independent of activation by thymidine kinase and insensitive to degradation by phosphorolytic enzymes*; Biochem. Pharmacol.; 2011, 82, 441-452).

Protide derivatives of purine nucleosides such as clofarabine and deoxyadenosine and related compounds have also shown excellent activity in vitro against a range of solid tumors, leukaemias and lymphomas (see WO2006/100439 and WO2016/083830 (PCT/GB2015/053628)). Deoxyadenosine itself is not a particularly potent anticancer agent.

Unfortunately, protides are often extremely lipophillic and thus poorly water soluble, and the ionisable moieties, tend to have calculated pKa values which lie outside the pH range suitable for parenteral administration. Many are essentially insoluble in water, regardless of salt content or pH within physiological ranges, and this puts limitations on the development of clinically acceptable methods for delivering the compounds at sufficiently high dosages for effective treatment.

It is an aim of certain embodiments of this invention to provide a pharmaceutical formulation of protides that delivers an effective dose.

It is an aim of certain embodiments of this invention to provide a stable pharmaceutical formulation of protides. For intravenous administration, suitable infusion formulations typically should be stable for greater than 30 minutes and up to 48 hours. Typically, for intravenous administration the formulation should be stable both to precipitation of the protide and to degradation of the protide.

It is an aim of certain embodiments of this invention to provide a pharmaceutical formulation of the protide which delivers an effective dose intravenously.

It is an aim of certain embodiments of this invention to provide a parenteral formulation of the protide which can be administered in either a peripheral vein or via a Central Venous Access Device (CVAD). Thus, it is an aim of certain embodiments of this invention to provide a formulation which has an osmolarity and pH that are acceptable for administration via a peripheral vein. It may be that the osmolarity and pH are such that the level of pain experienced by the patient is acceptable.

Certain embodiments of this invention satisfy some or all of the above aims.

BRIEF SUMMARY OF THE DISCLOSURE

In accordance with a first aspect of the present invention there is provided a pharmaceutical formulation comprising:
 a protide;
 a polar aprotic solvent; and
 optionally one or more pharmaceutically acceptable excipients;
 wherein the protide is not gemcitabine-[phenyl-benzoxy-L-alaninyl)]-phosphate (NUC-1031).

The polar aprotic solvent may be selected from dimethylacetamide (DMA) dimethylsulfoxide (DMSO) and N-methypyrrolidone (NMP). Preferably, the polar aprotic solvent is DMA. In an alternative preferred embodiment, the polar aprotic solvent is NMP. For certain protides, DMA offers the best solubility profile of those tested. For others, NMP may offer the best solubility profile.

A polar aprotic solvent is a solvent molecule of which comprise at least one heteroatom (e.g. O, N or S) but which does not have a hydrogen atom attached to the heteroatom or, where more than one heteroatom, any of the heteroatoms in the molecule. The polar aprotic solvent (e.g. DMA, DMSO or NMP) may be pharmaceutical grade. The polar aprotic solvent (e.g. DMA) may be the administration vehicle or it may be that the formulation is diluted before use with an administration vehicle which provides desirable characteristics. Thus, the formulation may be ready for infusion and have the polar aprotic solvent (e.g. DMA) as a major component; or it may be a formulation which has the polar aprotic solvent (e.g. DMA) as a major component and is intended to be diluted before administration to generate a formulation which is ready for infusion and has the polar aprotic solvent (e.g. DMA) only as a minor component; or it may be a formulation which is ready for infusion, has the polar aprotic solvent (e.g. DMA) only as a minor component and results from the dilution of a formulation in which polar aprotic solvent (e.g. DMA) is a major component. Thus, the polar aprotic solvent (e.g. DMA) may represent from 0.1% v/v to 100% v/v of the formulation.

Very few pharmaceutically acceptable solvents dissolve sufficient quantities of protides to deliver a therapeutically effective dose intravenously. Of those that do, many do not form stable solutions and protides will tend to precipitate out. The inventors have surprisingly found that solvents which do generate a stable solution are generally polar aprotic solvents, for example DMA, DMSO and NMP. Of those solvents that have been found to be capable of dissolving protides, the inventors have found that certain polar aprotic solvents, and in particular DMA either on its own or in conjunction with other solubilizers, are particularly able to hold certain protides in solution at a concentration necessary to deliver the required dose when that solution is diluted with an aqueous vehicle. For other protides, NMP was found to be the most effective at holding the protide in solution when that solution is diluted with an aqueous vehicle.

Thus, the use of polar aprotic solvents, and in particular DMA, provides an advantage over other formulation solvents which, surprisingly, makes it an excellent medium for delivering protides to patients in a practical and therapeutically effective manner.

The formulation of the invention may be for dilution by a predetermined amount shortly before administration, i.e. up to 48 hours (e.g. up to 24, 12 or 2 hours) before administration.

The formulation may also comprise one or more pharmaceutically acceptable solubilizers, e.g. a pharmaceutically acceptable non-ionic solubilizers. Solubilizers may also be called surfactants. Illustrative solubilizers include polyethoxylated fatty acids and fatty acid esters and mixtures thereof. Suitable solubilizers include polyethoxylated castor oil (e.g. that sold under the trade name Kolliphor® ELP); or polyethoxylated stearic acid (e.g. that sold under the trade names Solutol® or Kolliphor® HS15); or polyethoxylated (e.g. polyoxyethylene (20)) sorbitan monooleate, (e.g. that are sold under the trade names Polysorbate 80 or Tween® 80). Tween® 80, a polyethoxylated sorbitan monooleate, for example, has been shown to be particularly effective in formulations of NUC-7738.

In certain preferred embodiments, the formulation comprises more than one pharmaceutically acceptable solubilizer. Formulations comprising more than one solubilizer have been found to be particularly effective in formulations of NUC-3373.

The formulation may also comprise an aqueous vehicle. The formulation of the invention may be ready to administer, in which case it will typically comprise an aqueous vehicle.

The formulation may be for parenteral, e.g. for intravenous, subcutaneous or intramuscular administration. Preferably, the formulation is for intravenous administration. The administration may be through a CVAD or it may be through a peripheral vein.

The total dose of protide in a formulation suitable for administration will typically be from 250 mg to 5 g, from 250 mg to 3 g, from 500 mg to 2 g or from 1 g to 1.5 g.

While the formulations of the invention are preferably for parenteral administration, certain embodiments of the invention may also be administered orally.

In a second aspect of the invention is provided a pharmaceutical formulation comprising:
a protide;
a polar aprotic solvent (e.g. DMA); and
optionally one or more pharmaceutically acceptable excipients;
wherein the formulation is for medical use;
wherein the protide is not gemcitabine-[phenyl-benzoxy-L-alaninyl)]-phosphate.

In a third aspect of the invention is provided a pharmaceutical formulation comprising:
a protide;
a polar aprotic solvent (e.g. DMA); and
optionally one or more pharmaceutically acceptable excipients;
wherein the formulation is for use in treating cancer;
wherein the protide is not gemcitabine-[phenyl-benzoxy-L-alaninyl)]-phosphate.

The cancer may be a cancer selected from: pancreatic cancer, breast cancer, ovarian cancer, bladder cancer, colorectal cancer, lung cancer, bladder cancer, prostate cancer, cholangiocarcinoma, renal cancer, cervical cancer, thymic cancer, a cancer of an unknown primary origin, lymphoma or leukaemia.

Stock Solution Formulations

It may be that the polar aprotic solvent (e.g. DMA) represents 30% or more by volume of the formulation. Thus, it may be that the polar aprotic solvent (e.g. DMA) represents 50% or more, e.g. 60% or more by volume of the formulation. The polar aprotic solvent (e.g. DMA) may represent 95% or less by volume of the formulation, e.g. 90% or less. The formulation may also comprise an aqueous vehicle (e.g. saline). The aqueous vehicle may be present in 50% or less by volume of the formulation, e.g. 30% or less by volume of the formulation. Typically the aqueous vehicle (e.g. saline) will represent 5% or more, e.g. 10% or more, by volume of the formulation.

It may be that the concentration of the protide in the formulation solvent(s) is 1 g or less per mL. It may be that the concentration of the protide in the formulation solvent(s) is 500 mg or less per mL. It may be that the concentration 100 mg or more per mL. Preferably, the concentration is from 200 mg to 300 mg, e.g. from 225 mg to 275 mg, e.g. about 250 mg, per mL.

Certain preferred formulations comprise:
from 30% to 95% by volume DMA;
from 5% to 50% by volume aqueous vehicle; and
from 100 mg to 400 mg (e.g. from 100 mg to 300 mg) per mL protide.

More preferred formulations comprise:
from 70% to 90% by volume DMA;
from 10% to 30% by volume aqueous vehicle (e.g. saline); and from 200 mg to 300 mg per mL protide.

The formulations described in the previous four paragraphs, in which the polar aprotic solvent (e.g. DMA) is present as a major component may be for administering (e.g. by infusion or injection) the formulation without it being diluted prior to said administration. They may, for example, be for administration through a Central Venous Administration Device (CVAD). When administered via a CVAD, the formulation is typically not diluted.

Alternatively, these formulations may be stock solutions which are diluted prior to use to form a formulation suitable for administration, e.g. through a peripheral vein.

Surfactant Solution Formulations

It may be that the polar aprotic solvent (e.g. DMA) represents 10% or more, e.g. 20% or more by volume of the formulation. Thus, it may be that the polar aprotic solvent (e.g. DMA) represents 80% or less, e.g. 70% or less by volume of the formulation. The polar aprotic solvent (e.g. DMA) may represent 55% or less by volume of the formulation. The formulation may also comprise one or more solubilizers (e.g. one or more polyethoxylated fatty acids). The one or more solubilizers may represent 70% or less by volume of the formulation, e.g. 60% or less by volume of the formulation. Typically the one or more solubilizers will represent 20% or more, e.g. 35%, by volume of the formulation. The formulation may also comprise an aqueous vehicle, e.g. in an amount from 1% to 15% by volume or from 5% to 12% by volume.

It may be that the concentration of the protide in the formulation solvent(s) is 200 mg or less per mL, e.g. 150 mg or less or 130 mg or less. It may be that the concentration is 40 mg or more per mL, e.g. 60 mg or more. Preferably, the concentration is from 70 mg to 120 mg per mL, e.g. about 100 mg per mL.

Certain preferred formulations comprise:
from 20% to 70% by volume DMA;
from 20% to 70% by volume solubilizer or solubilizers; and
from 50 mg to 150 mg per mL protide. The formulation may also comprise an aqueous vehicle, e.g. in an amount from 1% to 15% by volume.

Certain particularly preferred formulations comprise:
from 30% to 60% by volume DMA;
from 10% to 35% by volume a first solubilizer;
from 10% to 35% by volume a second solubilizer;
from 2% to 15% an aqueous vehicle; and
from 50 mg to 150 mg per mL protide. The first solubilizer may be a polyethoxylated castor oils (e.g. that sold under the trade name Kolliphor® ELP). The second solubilizer may be a polyethoxylated sorbitan monooleate (e.g. that sold under the trade name Tween® 80).

The formulation may comprise:
from 35% to 50% by volume DMA;
from 15% to 30% by volume the first solubilizer;
from 15% to 30% by volume the second solubilizer;
from 5% to 12% an aqueous vehicle; and
from 50 mg to 150 mg per mL protide.

The surfactant solutions formulations described in the previous five paragraphs, in which the polar aprotic solvent (e.g. DMA) is present as a major component are typically diluted with an aqueous vehicle prior to administration. They are typically prepared from the stock solutions mentioned above before being further diluted ready for administration. Once diluted, they may be administered through a peripheral vein.

These formulations may be formed by diluting a stock solution formulation that does not contain any solubilizers with a solution which does contain solubilizers. Protides can degrade in the presence of certain solubilizers.

Infusion Solution Formulations

It may be that the polar aprotic solvent (e.g. DMA) represents 0.1% or more, e.g. 0.5% or more or 1% or more by volume of the formulation. Thus, it may be that DMA represents 12% or less, e.g. 10% or less or 8% or less by volume of the formulation. The formulation may also comprise an aqueous vehicle (e.g. saline or WFI). The aqueous vehicle may be present in 99.5% or less by volume of the formulation, e.g. 99% or 98% or less by volume of the formulation. Typically the aqueous vehicle will represent 80% or more, e.g. 95% or more, by volume of the formulation. The formulation may also comprise one or more solubilizers (e.g. one or more polyethoxylated fatty acids). The one or more solubilizers may present in 12% or less by volume of the formulation, e.g. 10% or less or 8% or less by volume of the formulation. Typically the one or more solubilizers will be present in 0.1% or more, e.g. 0.5% or more or 1% or more, by volume of the formulation.

It may be that the concentration of the protide in the formulation solvent(s) is 15.0 mg or less per mL or 12.0 mg or less per mL, e.g. 10.0 mg or less or 8 mg or less per mL. It may be that the concentration is 1.0 mg or more per mL, e.g. 2.0 mg or more. Preferably, the concentration is from 2.5 mg to 12 mg per mL, e.g. from 3 mg to 11 mg per mL.

Certain preferred formulations comprise:
from 0.1% to 10% by volume DMA;
from 0.1% to 10% by volume solubilizer or solubilizers;
from 85% to 99% by volume aqueous vehicle; and
from 2.0 mg to 12.0 mg per mL protide.

Certain particularly preferred formulations comprise:
from 1% to 8% by volume DMA;
from 0.5% to 4% by volume a first solubilizer;
from 0.5% to 4% by volume a second solubilizer;
from 85% to 99% by volume aqueous vehicle; and
from 2.0 mg to 12.0 mg per mL protide. The first solubilizer may be a polyethoxylated castor oil (e.g. that sold under the trade name Kolliphor® ELP). The second solubilizer may be a polyethoxylated sorbitan monooleate (e.g. that sold under the trade name Tween® 80).

The infusion solution formulations described in the previous four paragraphs, in which the polar aprotic solvent (e.g. DMA) is present as a minor component, will typically have been prepared by diluting a concentrated solution of the protide with the aqueous vehicle up to 48 hours prior to administration. Said concentrated solution may be either a solution of the protide in a polar aprotic solvent (see under the heading 'stock solution formulation' above) a solution of the protide in mixture of a polar aprotic solvent and a solubilizer (see under the heading 'surfactant solution formulation' above). These formulations in which the polar aprotic solvent (e.g. DMA) is present as a minor component may be administered through a peripheral vein. The low concentrations of the polar aprotic solvent (e.g. DMA) in said formulations mean that they tend not to cause pain upon peripheral administration.

Methods of Treatment and Kits

In a fourth aspect of the invention is provided a method of treating cancer, the method comprising administering to a subject in need thereof a pharmaceutical formulation comprising:
a protide;
a polar aprotic solvent (e.g. DMA); and
optionally one or more pharmaceutically acceptable excipients;
wherein the protide is not gemcitabine-[phenyl-benzoxy-L-alaninyl)]-phosphate.

The method may comprise the steps of;
diluting a solution comprising the protide, a polar aprotic solvent (e.g. DMA) and optionally one or more pharmaceutically acceptable excipients with an aqueous vehicle to provide a formulation for infusion or injection; and administering the formulation for infusion or injection to the subject by infusion or injection.

The method may comprise the steps of;

diluting a first solution comprising the protide and a polar aprotic solvent (e.g. DMA) and optionally an aqueous vehicle with a second solution comprising a polar aprotic solvent (e.g. DMA) and one or more solubilizers to form a third solution ("surfactant solution formulation");

diluting the third solution with an aqueous vehicle to provide a fourth solution (infusion solution formulation'); and administering the fourth solution to the subject by infusion or injection.

The second solution may comprise more than one solubilizer. Typically, the second formulation will not comprise a pharmaceutically active substance.

The or each dilution may be by a predetermined amount. The second solution may be called a 'diluent solution'.

The first solution may be a formulation of the first aspect (see under the heading 'stock solution formulation' above). Likewise, the third solution may be a formulation of the first aspect (see under the heading 'surfactant solution formulation' above). Likewise, the fourth solution may be a formulation of the first aspect (see under the heading 'infusion solution formulation' above).

The fourth solution may be administered via a CVAD. Preferably, however, the fourth formulation is administered via a peripheral vein.

The first solution may comprise:
from 30% to 95% by volume DMA;
from 5% to 50% by volume aqueous vehicle; and
from 100 mg to 400 mg (e.g. from 100 mg to 300 mg) per mL protide; and The second solution may comprise:
from 10% to 50% by volume DMA;
from 20% to 60% by volume a first solubilizer;
from 20% to 60% by volume a second solubilizer.

It may be that the administration step is carried out up to 48 hours (e.g. up to 12 or 2 hours) after the dilution step, e.g. the second dilution step to form the fourth solution.

In a fifth aspect of the invention is provided a kit, the kit comprising:

a first formulation comprising the polar aprotic (e.g. DMA) and the protide and optionally an aqueous vehicle;

a second formulation comprising the polar aprotic solvent and one or more solubilizers;

wherein the protide is not gemcitabine-[phenyl-benzoxy-L-alaninyl)]-phosphate.

Thus, the kit may comprise:
a first formulation comprising:
from 30% to 95% by volume DMA;
from 5% to 50% by volume aqueous vehicle; and
from 100 mg to 400 mg (e.g. from 100 mg to 300 mg) per mL a protide; and
a second formulation comprising:
from 10% to 50% by volume DMA;
from 20% to 60% by volume a first solubilizer;
from 20% to 60% by volume a second solubilizer.

Typically the second formulation will not comprise any active. The kit of the fifth aspect is useful for the preparation of formulations suitable for peripheral administration. The first formulation is diluted with the second formulation up to 48 h, e.g. up to 24 h before administration to form a third formulation. The third formulation is further diluted with an aqueous vehicle before administration to the desired concentration to form the formulation which is used administered by infusion or injection to the patient. In order to achieve formulations for peripheral administration which are stable with respect to precipitation of the protide, it is typically desirable to include solubilizers. However, protides can be prone to degradation in the presence of such solubilizers. Thus, a two stage dilution method is, in certain embodiments of the invention, the preferable means by which formulations for peripheral administration are achieved.

The method may comprise:

flushing a CVAD with a first portion of a first solution, the first solution comprising a polar aprotic solvent (e.g. DMA) and an aqueous vehicle;

administering a second formulation to the patient via the CVAD, the second formulation comprising the polar aprotic solvent, the aqueous vehicle and the protide; and optionally flushing the CVAD with a second portion of the first formulation.

Preferably, the relative amounts of the polar aprotic solvent and the aqueous vehicle in the first formulation are the same as the relative amounts in the second formulation.

Thus, the method of treatment may comprise:

flushing a CVAD with a first portion of a first solution, the first solution comprising: from 30% to 95% by volume DMA;
from 5% to 50% by volume aqueous vehicle; and
administering a second formulation to the patient via the CVAD, the second formulation comprising:
from 30% to 95% by volume DMA;
from 5% to 50% by volume aqueous vehicle; and
from 100 mg to 400 mg (e.g. from 100 mg to 300 mg) per mL protide; and
optionally flushing the administration device with a second portion of the first formulation. Typically, the first formulation will not comprise an active.

In a sixth aspect of the invention is provided a kit, the kit comprising:

a first solution comprising a polar aprotic solvent (e.g. DMA) and an aqueous vehicle; and a second formulation comprising the polar aprotic solvent, the aqueous vehicle and the protide;

wherein the protide is not gemcitabine-[phenyl-benzoxy-L-alaninyl)]-phosphate.

Thus, the kit may comprise:
a first formulation comprising:
from 30% to 95% by volume DMA;
from 5% to 50% by volume aqueous vehicle; and
a second formulation comprising:
from 30% to 95% by volume DMA;
from 5% to 50% by volume aqueous vehicle; and
from 100 mg to 400 mg (e.g. from 100 mg to 300 mg) per mL protide.

The first formulation will typically not comprise a pharmaceutically active substance. Thus, it will typically not comprise the protide. The first formulation may be provided in two separate vessels or in a single vessel.

The kit of the sixth aspect of the invention is useful for the intravenous administration of a protide via a CVAD. The CVAD is flushed with the first formulation prior to administration of the second formulation. This mitigates the risk of precipitation of the protide in or at the entrance to the intravenous administration apparatus, i.e. the CVAD, by avoiding the direct contact of the active formulation with aqueous media (e.g. a saline flushing solution). The CVAD may also be flushed with the first formulation after administration of the second formulation. This further prevents precipitation.

Methods of Preparing Formulations

In a fifth aspect of the invention is provided a method of preparing a pharmaceutical formulation of a protide for infusion or injection, the method comprising:

diluting a solution comprising the protide, a polar aprotic solvent (e.g. DMA) and optionally one or more pharmaceutically acceptable excipients with an aqueous vehicle to provide the formulation for infusion or injection;

wherein the protide is not gemcitabine-[phenyl-benzoxy-L-alaninyl)]-phosphate.

The dilution may be by a predetermined amount.

The starting solution may be a formulation of the first aspect (see under the heading 'stock solution formulations' and 'surfactant solution formulations'). Likewise, the formulation for infusion or injection may be a formulation of the first aspect (see under the heading 'infusion solution formulation' above). It may be that the administration step is carried out up to 48 hours (e.g. up to 12 or 2 hours) after the dilution step.

The aqueous vehicle may be selected from saline (e.g. 0.9% saline or 0.45% saline), glucose solution and water for infusion (WFI). The aqueous vehicle may be WFI. Alternatively, the aqueous vehicle may be 0.9% saline.

The osmolarity of the infusion solution is critically dependent on the dose required together with the volume and type of aqueous medium used, (i.e. the amount of surfactant solution used in the saline, and the % saline (0.45 or 0.9%)). Where the formulation is for administration via a peripheral vein, it may be that the aqueous vehicle is selected such that, at the desired dose and volume, the osmolarity of the infusion solution is between 200 mosm/L and 600 mosm/L. Preferably, where the formulation is for administration via a peripheral vein, the aqueous vehicle is selected such that the infusion solution is substantially isotonic with blood (e.g. the osmolarity of the infusion solution is from 250 mosm/L to 400 mosm/L).

The aqueous vehicle may comprise one or more pharmaceutically acceptable solubilizers (also known as a surfactants), e.g. a pharmaceutically acceptable non-ionic solubilizer. An exemplary solubilizer is polyoxyethylene (20) sorbitan monooleate (marketed as Tween® 80).

Protides

The formulations and formulation methods described in this specification are suitable for the administration of any protide. NUC-1031 (gemcitabine-[phenyl-benzoxy-L-alaninyl)]-phosphate or, to give it its full chemical name: 2'-deoxy-2',2'-difluoro-D-cytidine-5'-O-[phenyl (benzoxy-L-alaninyl)] phosphate) is however explicitly excluded from the scope of this application.

The term 'protide' is readily understood in the art to mean an aryloxy α-amino acid ester phosphoramidate derivative of a nucleoside or nucleoside analogue. Thus, the protide may be a compound having a structure according to formula (I):

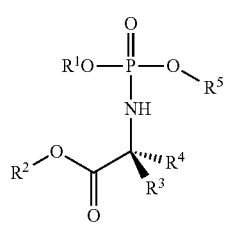

(I)

wherein $R^1$ is aryl;

$R^2$ is $C_1$-$C_{24}$-alkyl, $C_3$-$C_{24}$-alkenyl, $C_3$-$C_{24}$-alkynyl, $C_0$-$C_4$-alkylene-$C_3$-$C_6$-cycloalkyl or $C_0$-$C_4$-alkylene-aryl;

$R^3$ and $R^4$ are each independently selected from H, $C_1$-$C_6$-alkyl and $C_1$-$C_3$-alkylene-$R^6$; or wherein $R^3$ and $R^4$ together with the atom to which they are attached form a 3- to 6-membered cycloalkyl or heterocycloalkyl group;

$R^5$ is a nucleoside or nucleoside analogue;

$R^6$ is independently selected from aryl (e.g. phenyl), imidazole, indole, $SR^a$, $OR^a$, $CO_2R^a$, $CO_2NR^aR^a$, $NR^aR^b$ and $NH(=NH)NH_2$;

wherein any aryl group is either phenyl or naphthyl and wherein any phenyl or naphthyl group is optionally substituted with from 1 to 4 substituents selected from: halo, nitro, cyano, $NR^aR^a$, $NR^aS(O)_2R^a$, $NR^aC(O)R^a$, $NR^aCONR^aR^a$, $NR^aCO_2R^a$, $OR^a$; $SR^a$, $SOR^a$, $SO_3R^a$, $SO_2R^a$, $SO_2NR^aR^a$, $CO_2R^a$ $C(O)R^a$, $CONR^aR^a$, $CR^aR^aNR^aR^a$, $C_1$-$C_4$-alkyl, $C_2$-$C_4$-alkenyl, $C_2$-$C_4$-alkynyl and $C_1$-$C_4$-haloalkyl;

wherein $R^a$ is independently at each occurrence selected from: H and $C_1$-$C_4$-alkyl; and $R^b$ is independently at each occurrence selected from: H, and $C_1$-$C_4$-alkyl and $C(O)$—$C_1$-$C_4$-alkyl.

The nucleoside or nucleoside analogue may have the structure:

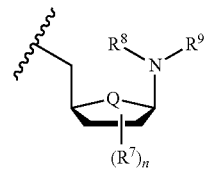

wherein:

Q is independently selected from O, $NR^a$ and $CH_2$;

$R^7$ is independently selected from: $OR^a$, $SR^a$, $NR^aR^b$; halo (e.g. F), cyano, $C_1$-$C_4$-alkyl, $C_2$-$C_4$-alkenyl and $C_2$-$C_4$-alkynyl;

$R^8$ and $R^9$ together with the nitrogen to which they are attached form a substituted pyrimidine or a substituted purine; wherein the purine or pyrimidine is substituted with from 1 to 5 groups selected from: $OR^a$, $SR^a$, $NR^aR^b$; halo, cyano, $C_1$-$C_4$-alkyl, $C_2$-$C_4$-alkenyl and $C_2$-$C_4$-alkynyl.

n is typically an integer from 0 to 4.

As will be readily appreciated by the skilled person, where a pyrimidine or purine is substituted with an OH group attached to a carbon atom neighbouring one of the nitrogen atoms in the pyrimidine or purine core, the pyrimidine or purine will typically exist primarily in the tautomeric form, i.e. one in which there is no double bond between the nitrogen and the neighbouring carbons but in which there is a double bond between the neighbouring carbon and the oxygen of the OH group. Said nitrogen may itself be substituted, e.g. with a $C_1$-$C_4$-alkyl group.

It may be that $R^8$ and $R^9$ together with the nitrogen to which they are attached form a substituted pyrimidine. It may be that $R^8$ and $R^9$ together with the nitrogen to which they are attached form a substituted purine.

The protide may be a compound having a structure according to formula (II):

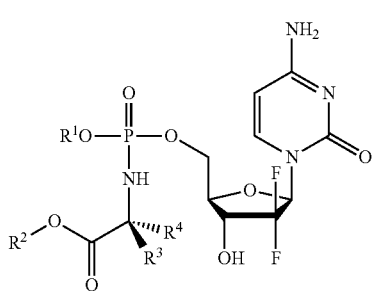

(II)

wherein

R¹, R², R³ and R⁴ are as described above for compounds of formula (I). NUC-1031 is excluded from the scope of this application and thus, for the absence of doubt, where the protide is a compound of formula (II), it cannot be the case that R¹ is unsubstituted phenyl, R² is unsubstituted benzyl, R³ is Me and R⁴ is H.

The protide may be a compound having a structure according to formula (III):

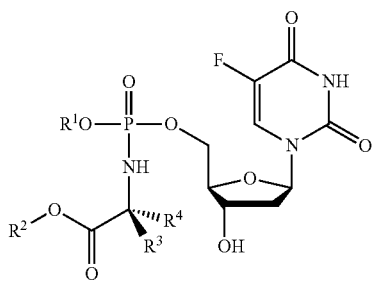

(III)

wherein

R¹, R², R³ and R⁴ are as described above for compounds of formula (I).

The protide may be a compound having a structure according to formula (IV):

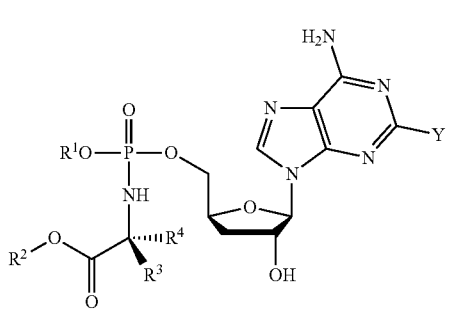

(IV)

wherein

R¹, R², R³ and R⁴ are as described above for compounds of formula (I); and wherein Y is independently selected from H, F, Cl and OMe. In certain preferred embodiments, Y is H. In other preferred embodiments, Y is F.

The Protide may be a compound having a structure according to formula (V):

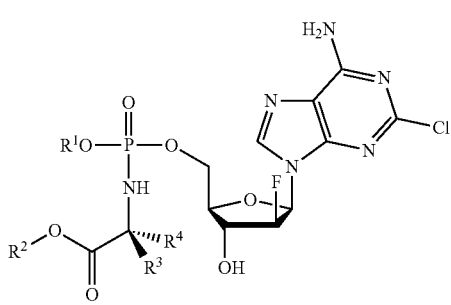

(V)

wherein

R¹, R², R³ and R⁴ are as described above for compounds of formula (I). Protides of formula (V) are derivatives of clofarabine.

The protide may be a compound having a structure according to formula (VI):

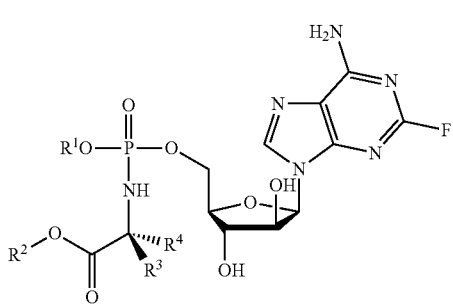

(VI)

wherein

R¹, R², R³ and R⁴ are as described above for compounds of formula (I). ProTides of formula (VI) are derivatives of fludarabine.

The protide may be a compound having a structure according to formula (VII):

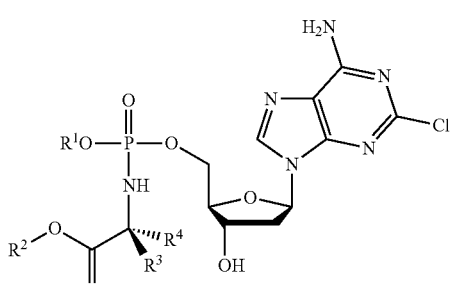

(VII)

wherein

R¹, R², R³ and R⁴ are as described above for compounds of formula (I). Protides of formula (VII) are derivatives of cladribine.

The following statements apply to protides of any of formulae (I) to (V). These statements are independent and interchangeable. In other words, any of the features described in any one of the following statements may (where chemically allowable) be combined with the features described in one or more other statements below. In particular, where a compound is exemplified or illustrated in this specification, any two or more of the statements below which describe a feature of that compound, expressed at any level of generality, may be combined so as to represent subject matter which is contemplated as forming part of the disclosure of this invention in this specification.

It may be that $R^1$ is substituted or unsubstituted phenyl. It may be that $R^1$ is substituted or unsubstituted naphthyl (e.g. 1-naphthyl). Preferably, $R^1$ is unsubstituted phenyl or unsubstituted naphthyl (e.g. 1-naphthyl). Thus, $R^1$ may be unsubstituted phenyl. Alternatively, $R^1$ may be or unsubstituted naphthyl (e.g. 1-naphthyl).

$R^2$ is preferably selected such that it comprises five or more carbon atoms. $R^2$ may therefore be selected such that it includes six or more carbon atoms. $R^2$ is preferably selected such that it comprises only carbon and hydrogen atoms. $R^2$ may be selected from $C_5$-$C_7$-cycloalkyl, $C_5$-$C_8$-alkyl and benzyl, optionally wherein said groups are unsubstituted. $R^2$ may be benzyl.

It may be that $R^4$ is H. It may be that $R^3$ is selected from $C_1$-$C_6$-alkyl and $C_1$-$C_3$-alkylene-$R^6$. It may be that $R^3$ is $C_1$-$C_4$-alkyl. It may be that $R^3$ is methyl.

Q is preferably 0.

n may be an integer from 1 to 3. n may be 1. n may be 2. n may be 3.

The protide is preferably a compound useful in the treatment of cancer.

Exemplary protides of formula (II) include the compounds described in WO 2005/012327, incorporated herein by reference. Exemplary protides of formula (II) include:

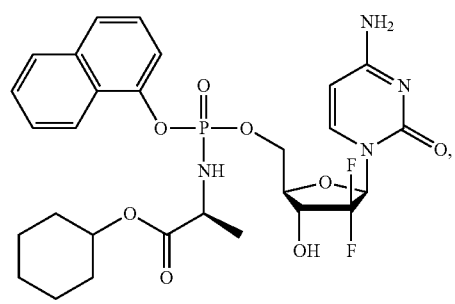

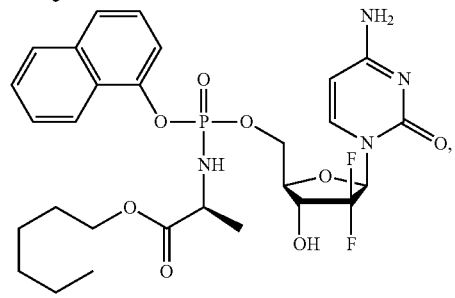

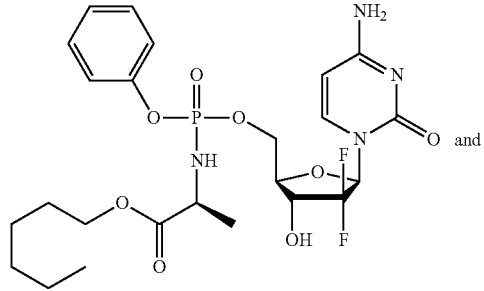

and

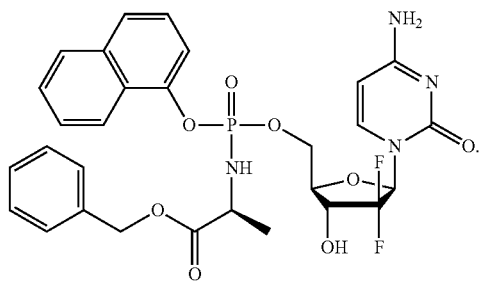

Exemplary protides of formula (III) include the compounds described in WO 2012/117246, incorporated herein by reference. Exemplary protides of formula (III) include:

(NUC-3373)

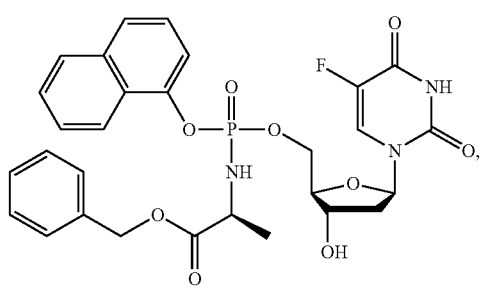

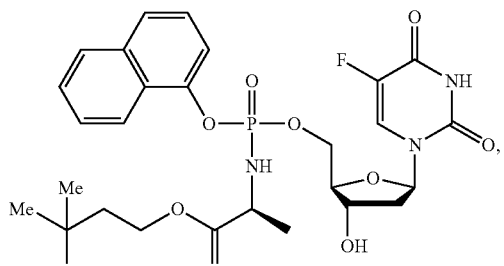

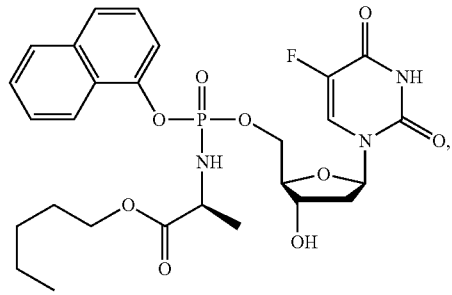

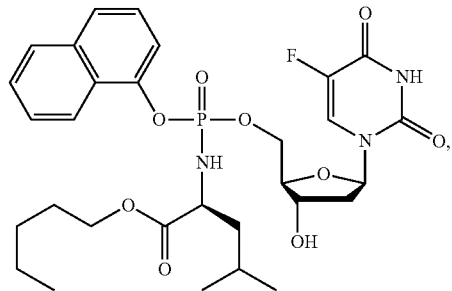

-continued
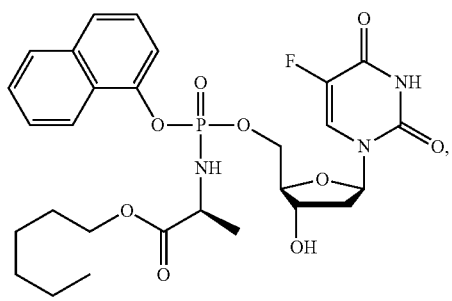
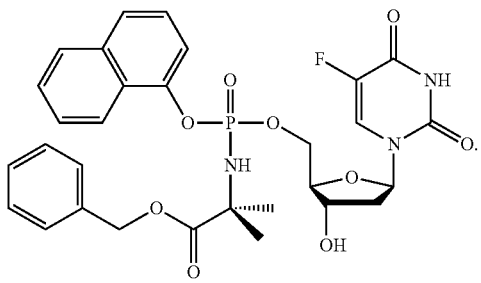
Exemplary protides of formula (IV) include the compounds described in WO2016/083830 (PCT/GB2015/053628), incorporated herein by reference. Exemplary protides of formula (IV) include:
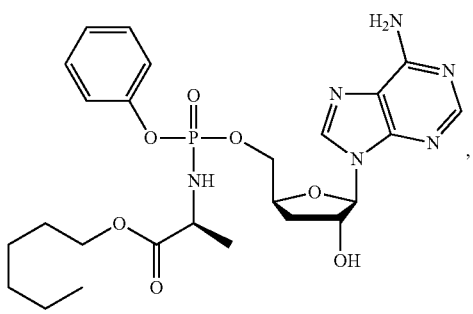
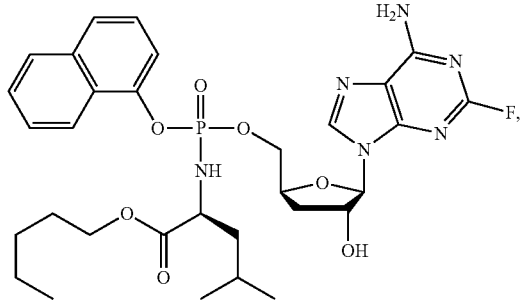
-continued
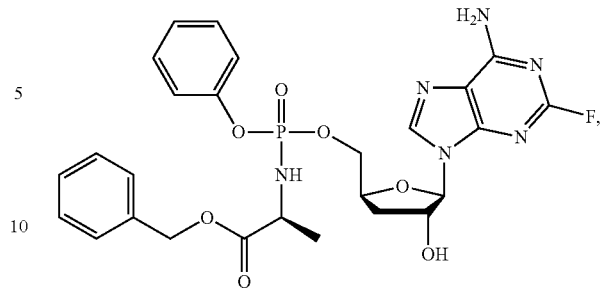
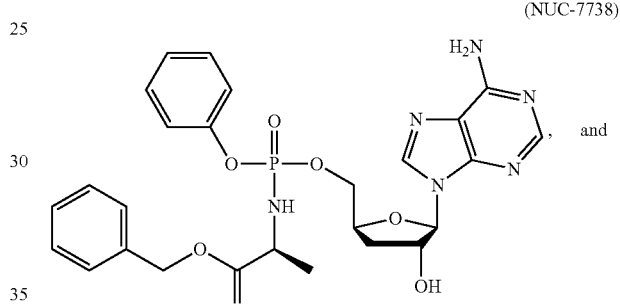
(NUC-7738)
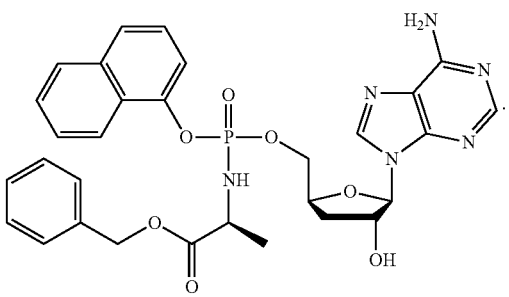 [SMILES: C[C@H](NP(=O)(OC[C@@H]1C[C@H](O)[C@H](n2cnc3c(N)ncnc32)O1)Oc1cccc2ccccc12)C(=O)OCc1ccccc1]
Exemplary protides of formulae (V), (VI) and (VII) include the compounds described in WO2006/100439. Exemplary protides of formula (V) include:
(CPF-448)

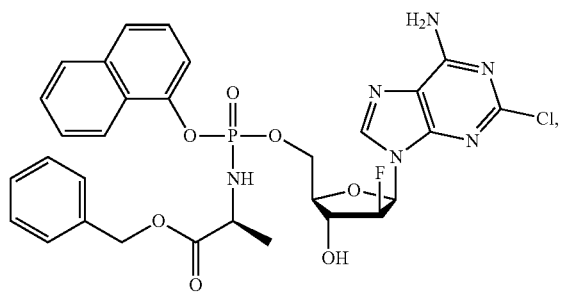

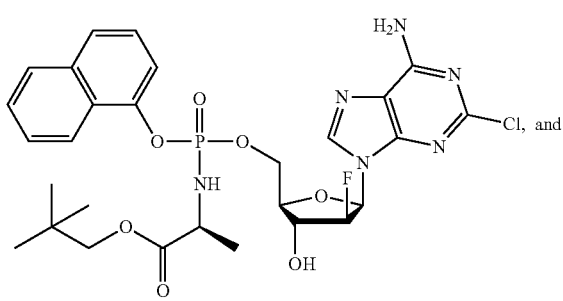

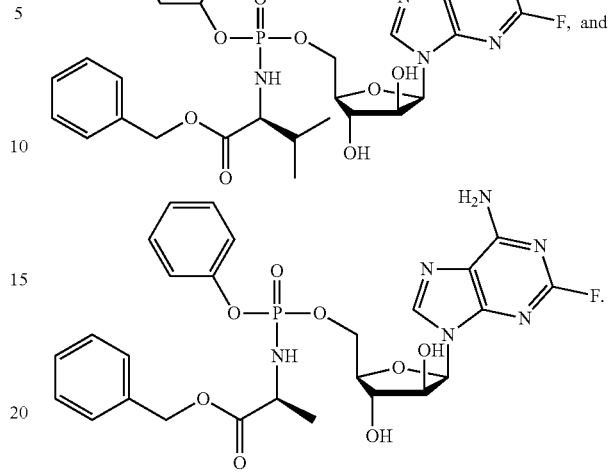

Exemplary protides of formula (VII) include:

Exemplary protides of formula (VI) include:

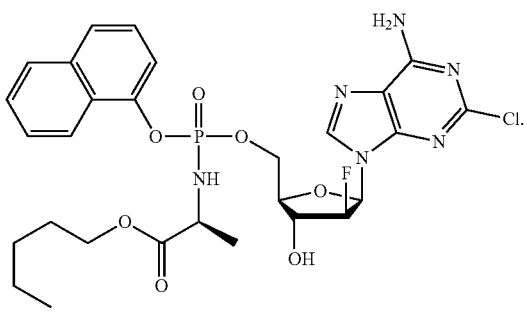

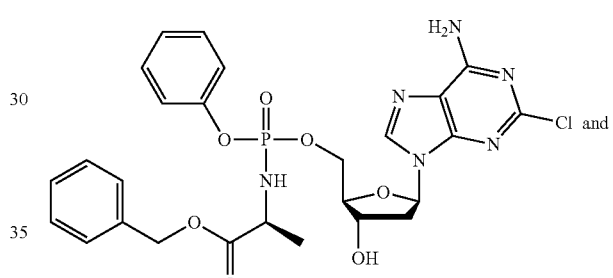

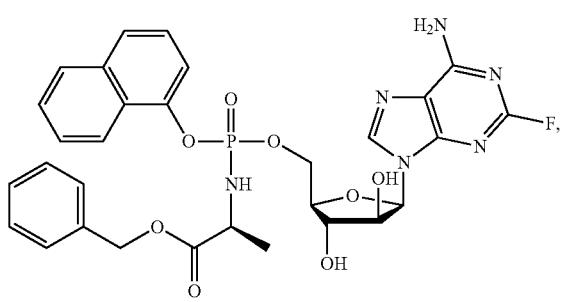

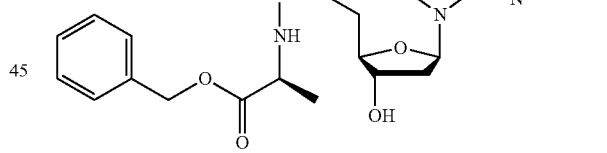

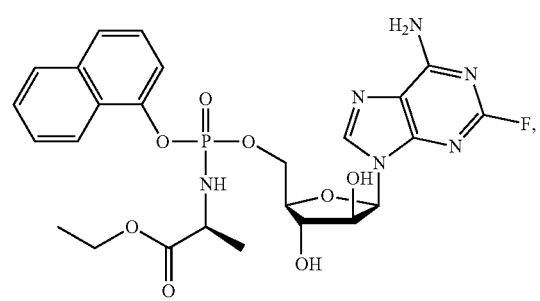

It may be that the protide is NUC-3373. It may be that the protide is NUC-3373 and the polar aprotic solvent is DMA. It may be that the protide is NUC-7738. It may be that the protide is NUC-7738 and the polar aprotic solvent is DMA. It may be that the protide is NUC-7738 and the polar aprotic solvent is NMP. It may be that the protide is CPF-448. It may be that the protide is CPF-448 and the polar aprotic solvent is DMA. It may be that the protide is CPF-448 and the polar aprotic solvent is NMP.

Protides typically comprise a chiral centre at the phosphorous atom. The protide may be present as a mixture of phosphate diastereoisomers, as the (S)-epimer at the phosphorus atom in substantially diastereomerically pure form or as the (R)-epimer at the phosphorus atom in substantially diastereomerically pure form. 'Substantially diastereomerically pure' is defined for the purposes of this invention as a diastereomeric purity of greater than about 90%. If present as a substantially diastereoisomerically pure form, the protide may have a diastereoisomeric purity of greater than 95%, 98%, 99%, or even 99.5%. Alternatively, the protide may be present as a mixture of phosphate diastereoisomers.

The (R)- and/or (S)-epimers of the protides can be obtained in substantially diastereomerically pure form by chromatography, e.g. HPLC optionally using a chiral column. Alternatively, the (R)- and/or (S)-epimers of the protides can be obtained in substantially diastereomerically pure form by crystallisation from an appropriate solvent or solvent system In a further alternative, the (R)- and/or (S)-epimers of the protides can be synthesised as an diastereomericaly pure form using a diastereoselective synthesis. It may be that any combination of these techniques could be used to provide a diastereomerically pure form, e.g. a diastereoselective synthesis followed by crystallisation or chromatography.

DETAILED DESCRIPTION

The term 'saline' is intended to refer to an aqueous solution of sodium chloride. Saline solutions of the present invention will typically be sterile and will typically be at a concentration suitable for use in parenteral administration. Suitable concentrations are up to 2 w/v % or up to 1 w/v %. To optimise osmolarity different concentrations of saline can be used in the formulations of the invention, e.g. 0.9% or 0.45%.

The formulations of the present invention can be used in the treatment of the human body. They may be used in the treatment of the animal body. In particular, the compounds of the present invention can be used to treat commercial animals such as livestock. Alternatively, the compounds of the present invention can be used to treat companion animals such as cats, dogs, etc.

The compounds in the formulations of the invention may be obtained, stored and/or administered in the form of a pharmaceutically acceptable salt. Suitable pharmaceutically acceptable salts include, but are not limited to, salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, malic, citric, lactic, mucic, gluconic, benzoic, succinic, oxalic, phenylacetic, methanesulphonic, toluenesulphonic, benzenesulphonic, salicylic, sulphanilic, aspartic, glutamic, edetic, stearic, palmitic, oleic, lauric, pantothenic, tannic, ascorbic and valeric acids. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulfate, hemioxalate and hemicalcium salts. Preferably, the compound of the invention are not in the form of a salt, i.e. they are in the form of the free base/free acid.

For the above-mentioned formulations of the invention the dosage administered will, of course, vary with the compound employed, the precise mode of administration, the treatment desired and the disorder indicated. Dosage levels, dose frequency, and treatment durations of compounds of the invention are expected to differ depending on the formulation and clinical indication, age, and co-morbid medical conditions of the patient. The size of the dose for therapeutic purposes of compounds of the invention will naturally vary according to the nature and severity of the conditions, the age and sex of the animal or patient and the route of administration, according to well known principles of medicine.

A pharmaceutical formulation typically takes the form of a composition in which active compounds, or pharmaceutically acceptable salts thereof, are in association with a pharmaceutically acceptable adjuvant, diluent or carrier. One such pharmaceutically acceptable adjuvant, diluent or carrier in the formulations of the invention is the polar aprotic solvent. Conventional procedures for the selection and preparation of suitable pharmaceutical formulations are described in, for example, "Pharmaceuticals—The Science of Dosage Form Designs", M. E. Aulton, Churchill Livingstone, 1988.

The formulations may be suitable for topical application (e.g. to the skin or bladder), for oral administration or for parenteral (e.g. intravenous administration).

Any solvents used in pharmaceutical formulations of the invention should be pharmaceutical grade, by which it is meant that they have an impurity profile which renders them suitable for administration (e.g. intravenous administration) to humans.

For oral administration the formulations of the invention may comprise the active compound admixed with an adjuvant or a carrier, for example, lactose, saccharose, sorbitol, mannitol; a starch, for example, potato starch, corn starch or amylopectin; a cellulose derivative; a binder, for example, gelatine or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatine, talcum and titanium dioxide. Alternatively, the tablet may be coated with a suitable polymer dissolved in a readily volatile organic solvent.

For the preparation of soft gelatine capsules, the active compounds may be admixed with, for example, a vegetable oil or polyethylene glycol. Hard gelatine capsules may contain granules of the compound using either the above-mentioned excipients for tablets. Also liquid or semisolid formulations of the active compounds may be filled into hard gelatine capsules.

Liquid preparations for oral application may be in the form of syrups or suspensions, for example, solutions containing the compound of the invention, the balance being sugar and a mixture of ethanol, water, glycerol and propylene glycol. Optionally such liquid preparations may contain colouring agents, flavouring agents, sweetening agents (such as saccharine), preservative agents and/or carboxymethylcellulose as a thickening agent or other excipients known to those skilled in art.

Preferably, however the formulations of the invention are for parenteral (e.g. intravenous) administration or for dilution to form a formulation for parenteral (e.g. intravenous) administration. For parenteral (e.g. intravenous) administration the active compounds may be administered as a sterile aqueous or oily solution. Preferably, the active compounds are administered as a sterile aqueous solution.

The pharmaceutical composition of the invention will preferably comprise from 0.05 to 99% w (percent by weight) protide, more preferably from 0.05 to 80% w protide, still more preferably from 0.10 to 70% w protide, and even more preferably from 0.10 to 50% w protide, all percentages by weight being based on total composition.

Cyclodextrins have been shown to find wide application in drug delivery (Rasheed et al, *Sci. Pharm.*, 2008, 76, 567-598). Cyclodextrins are a family of cyclic oligosaccharides. They act as a 'molecular cage' which encapsulates drug molecules and alters properties of those drug molecules such as solubility. Cyclodextrins comprise (α-1,4)-linked α-D-glucopyranose units. Cyclodextrins may contains 6, 7 or 8 glucopyranose units (designated α-, β- and γ-cyclodextrins respectively). Cyclodextrins used in pharmaceutical formulations are often β-cyclodextrins. The pendant hydroxyl groups can be alkylated with a $C_1$-$C_6$ substituted or unsubstituted alkyl group. Examples of cyclodextrins are α-cyclodextrin, β-cyclodextrin, γ-cyclodextrin, 2-hydroxypropyl-β-cyclodextrin (HP-β-CD), sulfobutylether β-cyclodextrin sodium salt, partially methylated β-cyclodextrin. The formulations of the invention may also comprise at least one cyclodextrin.

The term $C_m$-$C_n$ refers to a group with m to n carbon atoms.

The term "alkyl" refers to a linear or branched hydrocarbon group. An alkyl group is monovalent. For example, $C_1$-$C_6$-alkyl may refer to methyl, ethyl, n-propyl, iso-propyl, n-butyl, sec-butyl, tert-butyl, n-pentyl and n-hexyl. The alkyl groups are preferably unsubstituted.

The term "alkylene" refers to a linear hydrocarbon chain. An alkylene group is divalent. For example, $C_1$-alkylene may refer to a $CH_2$ group. $C_2$-alkylene may refer to —$CH_2CH_2$— group. The alkylene groups are preferably unsubstituted.

The term "haloalkyl" refers to a hydrocarbon chain substituted with at least one halogen atom independently chosen at each occurrence from: fluorine, chlorine, bromine and iodine. The halogen atom may be present at any position on the hydrocarbon chain. For example, $C_1$-$C_4$-haloalkyl may refer to chloromethyl, fluoromethyl, trifluoromethyl, chloroethyl e.g. 1-chloromethyl and 2-chloroethyl, trichloroethyl e.g. 1,2,2-trichloroethyl, 2,2,2-trichloroethyl, fluoroethyl e.g. 1-fluoromethyl and 2-fluoroethyl, trifluoroethyl e.g. 1,2,2-trifluoroethyl and 2,2,2-trifluoroethyl, chloropropyl, trichloropropyl, fluoropropyl, trifluoropropyl. A halo alkyl group may be a fluoroalkyl group, i.e. a hydrocarbon chain substituted with at least one fluorine atom.

The term "alkenyl" refers to a branched or linear hydrocarbon chain containing at least one carbon-carbon double bond. The double bond(s) may be present as the E or Z isomer. The double bond may be at any possible position of the hydrocarbon chain. For example, "$C_2$-$C_4$-alkenyl" may refer to ethenyl, allyl and butenyl. The alkenyl groups are preferably unsubstituted.

The term "alkynyl" refers to a branched or linear hydrocarbon chain containing at least one carbon-carbon triple bond. The triple bond may be at any possible position of the hydrocarbon chain. For example, "$C_2$-$C_6$-alkynyl" may refer to ethynyl, propynyl, butynyl. The alkynyl groups are preferably unsubstituted.

The term "cycloalkyl" refers to a saturated hydrocarbon ring system containing 3, 4, 5 or 6 carbon atoms. For example, "3- to 6-membered cycloalkyl" may refer to cyclopropyl, cyclobutyl, cyclopentyl, cyclohexyl. The cycloalkyl groups are preferably unsubstituted.

The term "heterocycloalkyl" may refer to a saturated monocyclic group comprising 1 or 2 heteroatoms independently selected from O, S and N in the ring system (in other words 1 or 2 of the atoms forming the ring system are selected from O, S and N). Examples of heterocycloalkyl groups include; piperidine, piperazine, morpholine, thiomorpholine, pyrrolidine, tetrahydrofuran, tetrahydrothiophene, tetrahydropyran, dihydropyran, dioxane, azepine. The heterocycloalkyl groups are preferably unsubstituted or substituted.

The present invention also includes formulations of all pharmaceutically acceptable isotopically-labelled forms of compound wherein one or more atoms are replaced by atoms having the same atomic number, but an atomic mass or mass number different from the atomic mass or mass number of the predominant isotope usually found in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds, for example, those incorporating a radioactive isotope, are useful in drug and/or substrate tissue distribution studies. The radioactive isotopes tritium, i.e. $^3$H, and carbon-14, i.e. $^{14}$C, and $^{18}$F are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Isotopically-labelled compounds can generally be prepared by conventional techniques known to those skilled in the art or by processes analogous to those described using an appropriate isotopically-labelled reagent in place of the non-labelled reagent previously employed.

The method of treatment or the formulation for use in the treatment of cancer, lymphoma or leukemia may involve, in addition to the formulations of the invention, conventional surgery or radiotherapy or chemotherapy. Such chemotherapy may include the administration of one or more other active agents.

Where a further active agent is administered as part of a method of treatment of the invention, such combination treatment may be achieved by way of the simultaneous, sequential or separate dosing of the individual components of the treatment. Such combination products employ the compounds of this invention within a therapeutically effective dosage range described hereinbefore and the one or more other pharmaceutically-active agent(s) within its approved dosage range.

Thus, the pharmaceutical formulations of the invention may comprise another active agent.

The one or more other active agents may be one or more of the following categories of anti-tumor agents:

(i) antiproliferative/antineoplastic drugs and combinations thereof, such as alkylating agents (for example cyclophosphamide, nitrogen mustard, bendamustin, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, pemetrexed, cytosine arabinoside, and hydroxyurea); antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); proteasome inhibitors, for example carfilzomib and bortezomib; interferon therapy; and topoisomerase inhibitors (for example epipodophyllotoxins like etoposide and teniposide, amsacrine, topotecan, mitoxantrone and camptothecin);

(ii) cytostatic agents such as antiestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents, for example dasatinib and bosutinib (SKI-606), and metalloproteinase inhibitors, inhibitors of urokinase plasminogen activator receptor function or antibodies to Heparanase;

(iv) inhibitors of growth factor function: for example such inhibitors include growth factor antibodies and growth factor receptor antibodies, for example the anti-erbB2 antibody trastuzumab [Herceptin™], the anti-EGFR antibody panitumumab, the anti-erbB1 antibody cetuximab, tyrosine kinase inhibitors, for example inhibitors of the epidermal growth factor family (for example EGFR family tyrosine kinase inhibitors such as gefitinib, erlotinib and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; modulators of protein regulators of cell apoptosis (for example Bcl-2 inhibitors); inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib, tipifarnib and lonafarnib), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor, kinase inhibitors; aurora kinase inhibitors and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™); thalidomide; lenalidomide; and for example, a VEGF receptor tyrosine kinase inhibitor such as vandetanib, vatalanib, sunitinib, axitinib and pazopanib;

(vi) gene therapy approaches, including for example approaches to replace aberrant genes such as aberrant p53 or aberrant BRCA1 or BRCA2;

(vii) immunotherapy approaches, including for example antibody therapy such as alemtuzumab, rituximab, ibritumomab tiuxetan (Zevalin®) and ofatumumab; interferons such as interferon α; interleukins such as IL-2 (aldesleukin); interleukin inhibitors for example IRAK4 inhibitors; cancer vaccines including prophylactic and treatment vaccines such as HPV vaccines, for example Gardasil, Cervarix, Oncophage and Sipuleucel-T (Provenge); and toll-like receptor modulators for example TLR-7 or TLR-9 agonists;

(viii) cytotoxic agents for example fludarabine (fludara), cladribine, pentostatin (Nipent™);

(ix) steroids such as corticosteroids, including glucocorticoids and mineralocorticoids, for example aclometasone, aclometasone dipropionate, aldosterone, amcinonide, beclomethasone, beclomethasone dipropionate, betamethasone, betamethasone dipropionate, betamethasone sodium phosphate, betamethasone valerate, budesonide, clobetasone, clobetasone butyrate, clobetasol propionate, cloprednol, cortisone, cortisone acetate, cortivazol, deoxycortone, desonide, desoximetasone, dexamethasone, dexamethasone sodium phosphate, dexamethasone isonicotinate, difluorocortolone, fluclorolone, flumethasone, flunisolide, fluocinolone, fluocinolone acetonide, fluocinonide, fluocortin butyl, fluorocortisone, fluorocortolone, fluocortolone caproate, fluocortolone pivalate, fluorometholone, fluprednidene, fluprednidene acetate, flurandrenolone, fluticasone, fluticasone propionate, halcinonide, hydrocortisone, hydrocortisone acetate, hydrocortisone butyrate, hydrocortisone aceponate, hydrocortisone buteprate, hydrocortisone valerate, icomethasone, icomethasone enbutate, meprednisone, methylprednisolone, mometasone parametasone, mometasone furoate monohydrate, prednicarbate, prednisolone, prednisone, tixocortol, tixocortol pivalate, triamcinolone, triamcinolone acetonide, triamcinolone alcohol and their respective pharmaceutically acceptable derivatives. A combination of steroids may be used, for example a combination of two or more steroids mentioned in this paragraph;

(x) targeted therapies, for example PI3Kd inhibitors, for example idelalisib and perifosine; or compounds that inhibit PD-1, PD-L1 and CAR T.

The one or more other active agents may also be antibiotic.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments.

The invention extends to any novel one, or any novel combination, of the features disclosed in this specification (including any accompanying claims, abstract and drawings), or to any novel one, or any novel combination, of the steps of any method or process so disclosed.

The readers attention is directed to all papers and documents which are filed concurrently with or previous to this specification in connection with this application and which are open to public inspection with this specification, and the contents of all such papers and documents are incorporated herein by reference.

The following abbreviations are used in this specification:

| | |
|---|---|
| DMA—dimethylacetamide | DMF—N,N-dimethylformamide |
| DMSO—dimethylsulfoxide | IPA—isopropyl alcohol |
| NMP—N-methylpyrroldinone | PEG—polyethylene glycol |

EXAMPLES

Example 1—Solubility of NUC-3373

The solubility of NUC-3373 (mixture of diastereoisomers) in a range of solvents is shown in Table 1.

TABLE 1

Solubility of NUC-3373 in a range of pharmaceutically relevant solvents

| Solvent | NUC-3373 (mg/mL) |
|---|---|
| Ethanol | 778 |
| Propylene glycol | 449 |
| PEG 400 | 422 |
| NMP | 705 |
| DMSO | 948 |
| DMA | 950 |
| Water | <2.0 |

As can readily be seen, the solubility of NUC-3373 in water is extremely low. Of the solvents tested, the polar aprotic solvents and particularly DMSO and DMA offered the best solubilities.

Example 2—Development of an Aqueous Formulation of NUC-3373

The successful development of the Diluent Solution to enable preparation of the NUC-1031 aqueous formulation prompted its development for an aqueous formulation of NUC-3373. An aqueous NUC-3373 formulation was developed by adding 6.7 ml of a 250 mg/ml solution of NUC-3373 in 80% DMA:20% 0.9% saline to 10 ml diluent solution to generate a 100 mg/ml NUC-3373 surfactant solution (see Table 4), prior to subsequent dilution into an infusion bag.

The clinical dose for NUC-3373 has yet to be established, but the estimated maximum dose may be up to 3,000 mg, which set the upper limit for the formulation development studies. Table 2 shows the volume of 100 mg/ml NUC-3373 surfactant solution that is required to be added to a 250 ml infusion bag for a variety of doses, and the resulting composition of the aqueous infusion solution.

TABLE 2

Composition of saline infusion solution across a variety of doses of NUC-3373.

| NUC-3373 Dose (mg) | 1,000 mg | | 2,000 mg | | 3,000 mg | |
|---|---|---|---|---|---|---|
| NUC-3373 Concentration | 3.85 mg/ml | | 7.41 mg/ml | | 10.72 mg/ml | |
| Surfactant solution volume | 10.0 ml | | 19.9 ml | | 29.9 ml | |
| Composition | | | | | | |
| DMA | 4.4 ml | 2% | 8.8 ml | 3% | 13.2 ml | 5% |
| KELP | 2.4 ml | 1% | 4.8 ml | 2% | 7.2 ml | 3% |
| Tw80 | 2.4 ml | 1% | 4.8 ml | 2% | 7.2 ml | 3% |
| Saline | 250.8 ml | 96% | 251.6 ml | 93% | 252.4 ml | 90% |
| Infusion volume | 260.0 ml | | 269.9 ml | | 279.9 ml | |

The stability of the 100 mg/ml NUC-3373 surfactant solution under two storage conditions (5° C. and 20° C.) has been shown to be stable for 48 hours at both condition (see Table 3).

TABLE 3

Stability of 100 mg/ml NUC-3373 surfactant solution.

| | 0 hours | | 8 hours | | 24 hours | | 48 hours | |
|---|---|---|---|---|---|---|---|---|
| | 5° C. | 20° C. | 5° C. | 20° C. | 5° C. | 20° C. | 5° C. | 20° C. |
| Assay content (mg/ml) | 105.5 | 104.8 | 102.5 | 100.7 | 103.7 | 99.1 | 102.4 | 99.4 |
| Purity (% area) | 96.1 | 96.2 | 96.2 | 96.1 | 96.1 | 96.1 | 96.1 | 96.2 |
| pH | 7.8 | 7.8 | 7.9 | 7.8 | 7.9 | 7.8 | 7.9 | 7.9 |
| Appearance | Clear and yellowish | | Clear and yellowish | | Clear and yellowish | | Clear and yellowish | |

The stability of the aqueous infusion solution was also evaluated using three different doses of NUC-3373 (1,000 mg, 2,000 mg and 3,000 mg) diluted in 250 ml 0.9% saline bags at two storage conditions (5° C. and 20° C.). The results shown in Tables 4, 5 and 6, demonstrate that the aqueous infusion solutions at all dose strengths are stable for up to 48 hours under both storage conditions.

TABLE 4

Stability of 1,000 mg NUC-3373 in 250 ml 0.9% saline infusion bag.

| | 0 hours | | 8 hours | | 24 hours | | 48 hours | |
|---|---|---|---|---|---|---|---|---|
| | 5° C. | 20° C. | 5° C. | 20° C. | 5° C. | 20° C. | 5° C. | 20° C. |
| Assay content NUC-3373 (mg/ml) | 3.7 | 3.9 | 3.6 | 3.7 | 3.6 | 3.7 | 3.6 | 3.8 |
| Total NUC-3373 (mg) | 960.9 | 1012.8 | 934.9 | 960.9 | 934.9 | 960.9 | 934.9 | 986.9 |
| Purity (% area) | 96.2 | 96.1 | 96.1 | 96.1 | 96.1 | 96.1 | 96.2 | 96.1 |
| pH | 5.5 | 5.6 | 5.6 | 5.5 | 5.6 | 5.8 | 5.5 | 5.5 |
| Osmolarity (mosm/L H20) | 457 | 462 | 450 | 459 | 456 | 462 | 451 | 455 |
| Appearance | Clear and colourless | | Clear and colourless | | Clear and colourless | | Clear and colourless | |

TABLE 5

Stability of 2,000 mg NUC-3373 in 250 ml 0.9% saline infusion bag.

| | 0 hours | | 8 hours | | 24 hours | | 48 hours | |
|---|---|---|---|---|---|---|---|---|
| | 5° C. | 20° C. | 5° C. | 20° C. | 5° C. | 20° C. | 5° C. | 20° C. |
| Assay content NUC-3373 (mg/ml) | 7.2 | 7.4 | 7.0 | 7.5 | 6.9 | 7.2 | 7.0 | 7.1 |
| Total NUC-3373 (mg) | 1946 | 2000 | 1892 | 2027 | 1865 | 1946 | 1892 | 1919 |
| Purity (% area) | 96.1 | 96.1 | 96.2 | 96.1 | 96.1 | 96.1 | 96.1 | 96.1 |
| pH | 5.5 | 5.5 | 5.5 | 5.5 | 5.5 | 5.5 | 5.4 | 5.4 |
| Osmolarity (mosm/L H20) | 639 | 646 | 637 | 633 | 638 | 639 | 635 | 632 |
| Appearance | Clear and colourless | | Clear and colourless | | Clear and colourless | | Clear and colourless | |

TABLE 6

Stability of 3,000 mg NUC-3373 in 250 ml 0.9% saline infusion bag.

| | 0 hours | | 8 hours | | 24 hours | | 48 hours | |
|---|---|---|---|---|---|---|---|---|
| | 5° C. | 20° C. | 5° C. | 20° C. | 5° C. | 20° C. | 5° C. | 20° C. |
| Assay content NUC-3373 (mg/ml) | 10.2 | 10.4 | 10.4 | 10.5 | 10.1 | 10.4 | 10.0 | 10.1 |
| Total NUC-3373 (mg) | 2857 | 2913 | 2913 | 2941 | 2829 | 2913 | 2801 | 2829 |
| Purity (% area) | 96.1 | 96.1 | 96.2 | 96.1 | 96.1 | 96.1 | 96.2 | 96.1 |
| pH | 5.5 | 5.5 | 5.5 | 5.5 | 5.5 | 5.5 | 5.6 | 5.4 |
| Osmolarity (mosm/L H20) | 831 | 818 | 823 | 812 | 825 | 817 | 821 | 812 |
| Appearance | Clear and colourless | | Clear and colourless | | Clear and colourless | | Clear and colourless | |

The pH and osmolarity of the 1,000 mg and 2,000 mg dose solutions in a 250 ml 0.9% saline bag are suitable for intravenous administration via either a CVAD or peripheral vein.

Aqueous Infusion Solutions

The stability studies described above used 250 ml 0.9% saline bags as the base infusion solution, however similar stability results have been demonstrated if alternative aqueous infusion solutions were used (e.g. Water for Injection (WFI), 0.45% saline) or the volume of the infusion bag was increased (e.g. 500 ml). Lower saline concentrations or increased volume of infusion do not affect the stability over 48 hours, and do not significantly alter the pH, and serve to reduce the osmolarity of the infusion solution. For example, using 0.45% saline or WFI reduces the osmolarity of the high dose NUC-3373 (10 mg/ml) from 812 mosm/l to 715 and 557 mosm/l $H_2O$ respectively, whereas increasing the volume of the 0.9% saline infusion bag from 250 ml to 500 ml at the high dose (3,000 mg) NUC-3373 infusion solution reduces the osmolarity from 812 mosm/l to 524 mosm/I. These alternative infusion solutions may make the high dose NUC-3373 aqueous based formulation suitable for peripheral vein infusion as well as CVAD infusion.

Example 3—Illustrative Description of a Formulation Methodology

A formulation methodology (see WO2015/198059 (PCT/GB2015/051858)) has been developed for the intravenous administration of protides. This methodology has been shown in clinical trials to be effective for NUC-1031 which has broadly the same solubility profile as NUC-3373 and NUC-7738. That methodology is as follows:

A 250 mg/mL solution of the protide (the S-epimer, the R epimer or a mixture thereof) is formed in an 80:20 (by volume) mixture of DMA and 0.9% saline. This stock solution formulation is typically sufficiently stable for long term storage and transport of protides.

This stock solution formulation can be administered to patients intravenously via a CVAD (e.g. a Hickman line, PICC line). The intravenous administration apparatus will typically be flushed with an 80:20 (by volume) mixture of DMA and 0.9% saline both before and after administration of the formulation comprising the protide. This helps mitigate the risk of any potential precipitation of protide in the intravenous administration apparatus on contact with the saline flush.

Alternatively, where intravenous administration using a saline bag infusion is the preferred method of administration, the stock solution formulation is diluted to 100 mg/mL with a diluent solution which is 20%:40%:40% mixture of DMA:Tween® 80:Kolliphor® ELP (e.g. 6.7 mL of 250 mg/ml protide in 80:20 DMA:0.9% saline is added to 10 mL of the DMA:Tween®80:Kolliphor® ELP diluent solution). The resultant (surfactant solution) formulation is typically stable for up to 5 days.

The infusion solution formulation is then prepared by diluting this surfactant solution formulation to the desired concentration with 0.9% saline.

For NUC-1031, solutions of either the S-isomer alone or a mixture of the R and S epimers at 4, 8 and 10 mg/mL have been shown to be stable (both to precipitation of NUC-1031 and to degradation of NUC-1031) for 48 hours after dilution of this formulation in both 0.45% and 0.9% saline at a range of pHs (4.5, 6.0 and 7.0), providing the mixtures were not stirred. The osmolarity of all of the NUC-1031 solutions has also been shown to be acceptable for peripheral administration.

In a clinical trial of NUC-3373, this administration methodology has allowed NUC-3373 to be successfully administered via a CVAD. Early results are that the infusion solutions of NUC-3373 prepared as described in this example have some efficacy in treating cancer.

Example 4—Solubility of NUC-7738

The solubility of NUC-7738 in a range of solvents is shown in Table 7.

TABLE 7

Solubility of NUC-7738 (mixture of diastereoisomers) in a range of solvents

| Solvent | NUC-7738 (mg/mL) |
|---|---|
| Ethanol | >667 |
| Propylene Glycol | >667 |
| DMSO | >667 |
| NMP | >667 |
| DMA | >667 |
| Heptane | <12 |
| ,butylmethylether | <11 |
| isopropylacetate | <9 |
| Water | <5.2 |
| 5% Tween in water | <11.8 |

As can readily be seen, the solubility of NUC-7738 in water is extremely low, even when the water incorporates a solubiliser. NUC-7738 is, however, soluble in polar solvents, including NMP, DMSO and DMA.

Example 5—Development of an Aqueous Formulation of NUC-7738

50 µL of a 100 mg/mL concentrate of NUC-7738 (mixture of diastereoisomers) in a range of solvents (DMA, DMSO, NMP, ethanol, benzyl alcohol) was mixed with 50 µL of Tween® 80 and added to 1.150 mL saline and the resultant solutions were checked by eye for precipitation of NUC-7738. Similarly a 50 µL concentrate of NUC-7738 (mixture of diastereoisomers) in Tween® 80 was mixed with 50 µL water for injection and then added to 1.150 mL saline. The results are shown in table 8.

TABLE 8

| Solvents | | | | | | | | |
|---|---|---|---|---|---|---|---|---|
| DMA | DMSO | NMP | EtOH | BnOH | TW80 | WFI | Saline | Appearance |
| 50 | | | | | 50 | | 1150 | Clear and limpid solution |
| | 50 | | | | 50 | | 1150 | Clear and limpid solution |
| | | 50 | | | 50 | | 1150 | Clear and limpid solution |
| | | | 50 | | 50 | | 1150 | White precipitate, milky solution |
| | | | | 50 | 50 | | 1150 | White precipitate, milky solution |
| | | | | | 50 | 50 | 1150 | White precipitate, milky solution |

Table 8 shows that DMSO, DMA and NMP are much more effective at retaining NUC-7738 in aqueous solution than other solvents, for example, ethanol in which NUC-7738 has good solubility in non-aqueous conditions. Even a solubiliser is not effective, in the absence of a polar aprotic solvent, at retaining NUC-7738 in solution in aqueous conditions.

The solutions prepared above were assayed for NUC-7738 content and purity on being formed and also after 48 h. Both the assay content and the purity were substantially unchanged after 48 h, indicating that the solutions were chemically and physically stable over this period.

In a further experiment, the minimum concentration of NUC-7738 in solvents that could be diluted with saline without precipitation was determined. Solutions of NUC-7738 (mixture of diastereoisomers) at various concentrations in NMP, DMSO and DMA were prepared and 100 µL of the solutions were added to 2.40 mL saline. The resultant aqueous solutions were observed for precipitation of NUC-7738. The results are provided in Table 9.

TABLE 9

| Concentrate solutions NUC-7738 | | | | | | | | |
| --- | --- | --- | --- | --- | --- | --- | --- | --- |
| NMP 100 mg/ml | NMP 50 mg/ml | NMP 25 mg/ml | DMSO 100 mg/ml | DMSO 50 mg/ml | DMSO 25 mg/ml | DMA 25 mg/ml | Saline | Appearance |
| 100 | | | | | | | 2400 | White insoluble precipitate from the first drop |
| | 100 | | | | | | 2400 | White insoluble precipitate from the first drop |
| | | 100 | | | | | 2400 | Clear and limpid solution |
| | | | 100 | | | | 2400 | White insoluble precipitate from the first drop |
| | | | | 100 | | | 2400 | White insoluble precipitate from the first drop |
| | | | | | 100 | | 2400 | White precipitate after addition of 100 µL |
| | | | | | | 100 | 2400 | White insoluble precipitate from the first drop |

As can be seen, the best solvent for retaining NUC-7738 in aqueous solution appeared to be NMP which provided a clear and limpid solution when a 25 mg/mL solution was diluted with saline.

What is claimed is:

1. A pharmaceutical stock solution to prepare a formulation for infusion to a human patient in need thereof comprising:
   100 or more mg/mL 5-fluoro-2'-deoxyuridine-5'-O-[1-naphthyl (benzoxy-L alaninyl)] phosphate (NUC-3373) or a pharmaceutically acceptable salt thereof; 30-95% by volume dimethyl acetamide (DMA); an aqueous vehicle, and optionally one or more pharmaceutically acceptable excipients.

2. The formulation of claim 1, wherein the formulation comprises between 30-95% DMA, and 5-50% aqueous vehicle.

3. The formulation of claim 2, wherein the aqueous vehicle is saline.

4. The formulation of claim 2, wherein the aqueous vehicle is water for injection.

5. The formulation of claim 1, wherein the formulation comprises a solubilizer.

6. The formulation of claim 5, wherein the formulation comprises two or more solubilizers.

7. The formulation of claim 5, wherein the solubilizer is a polyethoxylated fatty acid or a mixture thereof.

8. The formulation of claim 1, wherein the formulation comprises:
   from 20% to 55% by volume DMA;
   35% or more by volume a solubilizer or solubilizers; and
   from 100 to 400 mg per mL NUC-3373.

9. The formulation of claim 1, wherein the formulation is suitable for infusion by a central venous access device.

* * * * *